United States Patent [19]

Ogawa et al.

[11] Patent Number: 6,111,148
[45] Date of Patent: Aug. 29, 2000

[54] PROCESS FOR PRODUCING TERTIARY BUTYL ALCOHOL

[75] Inventors: Akira Ogawa; Kenichi Fujimoto; Yasutaka Nakashima, all of Otaka, Japan

[73] Assignee: Mitsubishi Rayon Co., Ltd., Tokyo, Japan

[21] Appl. No.: 09/449,675

[22] Filed: Nov. 30, 1999

Related U.S. Application Data

[63] Continuation-in-part of application No. PCT/JP98/05918, Dec. 25, 1998.

[30] Foreign Application Priority Data

Dec. 26, 1997 [JP] Japan ................................ 9-360599

[51] Int. Cl.$^7$ .................................................. C07C 29/06
[52] U.S. Cl. .......................... 568/899; 568/895; 568/896
[58] Field of Search .................... 568/899, 896, 568/895

[56] References Cited

U.S. PATENT DOCUMENTS

| | | | |
|---|---|---|---|
| 3,328,470 | 6/1967 | Kronig | 568/899 |
| 4,087,471 | 5/1978 | Bowman | 568/899 |
| 4,180,688 | 12/1979 | Imaizumi | 568/899 |
| 4,307,257 | 12/1981 | Sada | 568/899 |
| 4,760,202 | 7/1988 | Dettmer | 568/899 |

FOREIGN PATENT DOCUMENTS

| | | |
|---|---|---|
| 53-14044 | 5/1978 | Japan . |
| 53-20482 | 6/1978 | Japan . |
| 56-34643 | 4/1981 | Japan . |
| 56-10124 | 5/1981 | Japan . |
| 56-22855 | 5/1981 | Japan . |
| 56-87526 | 7/1981 | Japan . |
| 57-10853 | 3/1982 | Japan . |
| 57-108028 | 7/1982 | Japan . |
| 60-233024 | 11/1985 | Japan . |
| 61-229832 | 10/1986 | Japan . |

*Primary Examiner*—Michael L. Shippen
*Attorney, Agent, or Firm*—Oblon, Spivak, McClelland, Maier & Neustadt, P.C.

[57] ABSTRACT

A process for continuously producing tertiary butyl alcohol from water and a liquefied gas composed of isobutylene or an isobutylene-containing hydrocarbon using tertiary butyl alcohol as a solvent in the presence of a cation exchange resin in a series multistage reactor, wherein the reaction temperature in each reaction vessel of the series multistage reactor is adjusted to not more than 65° C., a part of the reaction mixture in the outlet of the first reaction vessel is returned to the inlet portion of the first reaction vessel at a circulation ratio of 1.8 to 10, and the weight ratio of the tertiary butyl alcohol to the liquefied gas in the inlet portion of the first reaction vessel is 0.5 to 3.5.

10 Claims, 1 Drawing Sheet

PROCESS FOR PRODUCING TERTIARY BUTYL ALCOHOL

CROSS-REFERENCE

The present invention is a continuation-in-part application of PCT/JP98/05918 filed Dec. 25, 1998, the content of which is herein incorporated by reference, which relies for priority upon the inventors' Japanese Patent Application No. 09-360599 filed Dec. 26, 1997, the content of which is also herein incorporated by reference.

BACKGROUND OF THE INVENTION

1. Field of the Invention

This invention relates to a process for continuously producing tertiary butyl alcohol (referred to hereinafter as TBA) from isobutylene and water using tertiary butyl alcohol as a solvent in the presence of a cation exchange resin in a series multistage reactor.

2. Description of the Background

Many methods for producing TBA by hydration reaction from isobutylene and water using an ion exchange resin catalyst have been known. Known are, for example, a method in which an organic acid is used as a solvent (JP-B-53-20,482, JP-B-53-14,044 and JP-B-56-22,855), a method in which a polar solvent is used (JP-A-56-34,643, JP-A-57-108,028, JP-A-56-87,526, JP-B-57-10,853, JP-A-56-10,124 and JP-A-60-233,024), a method in which TBA is used as a polar solvent (JP-B-57-10,853, JP-A-56-10,124 and JP-A-60-233,024) and a method in which the reaction is effected in a heterogeneous system without using a solvent (JP-A-54-27,507, JP-A-54-30,104, JP-A-54-30,105, JP-A-55-85,529 and JP-A-55-108,825).

However, the method in which an organic acid is used as a solvent has such problems that the TBA produced is reacted with the organic acid, which is the solvent, to produce a large amount of an organic acid ester as a by-product, so that the utilization of the starting materials is lowered and that in order to increase the utilization, an operation for hydrolyzing the organic acid ester produced as a by-product becomes necessary. In addition, there is also a problem that the method requires an expensive apparatus material resistant to corrosion with the organic acid used as the solvent.

The method in which other polar solvents than TBA are used can increase the yield by a combination of the solvent used with a reaction process; however, there are such problems that incidental facilities become necessary for separating TBA from the polar solvent and hence the equipment cost is increased.

In the method in which TBA is used as the solvent, the catalyst cannot be effectively utilized because the reaction liquid composed of the starting $C_4$ mixture, water and TBA forms a heterogeneous phase in the vicinity of the reactor inlet. Therefore, such measures have been taken that a large amount of TBA is added to the reaction system so that the reaction liquid forms a homogeneous phase and that a decanter and a distillation column are placed between plural reaction vessels. However, all the measures have such a problem that the service cost or the equipment cost becomes high. Moreover, a method in which the reaction is effected using a piston type reactor has been considered, but the reaction liquid is heterogeneous in the inlet portion of the reactor, so that the reaction does not proceed and it follows that the hydration reaction is accelerated by elevating the reaction temperature. Therefore, there is a problem that the amounts of isobutylene dimer, secondary butyl alcohol and the like produced as by-products are increased.

The method in which the reaction is effected in a heterogeneous system without using a solvent or the like is low in reaction rate, and hence, requires a larger reactor than other methods in order to secure the necessary production. Accordingly, when the method is carried out on a commercial scale, there is a problem that the equipment cost becomes high. Moreover, the above method has also a problem in that the amounts of isobutylene dimer or secondary butyl alcohol produced as by-products become large.

Since TBA is used as the starting material for producing methyl methacrylate by a gas phase catalytic oxidation or producing high purity isobutylene; as a gasoline additive; or the like, it is desirable that the amounts of isobutylene dimer, secondary butyl alcohol and the like produced as by-products are as small as possible.

SUMMARY OF THE INVENTION

Accordingly, the object of this invention is to provide a simple process for producing TBA at a high yield which process does not require expensive equipment materials and excessively large incidental facilities and can inhibit isobutylene dimer, secondary butyl alcohol and the like from being produced as by-products.

According to this invention, there is provided a process for continuously producing TBA from water and a liquefied gas composed of isobutylene or an isobutylene-containing hydrocarbon using TBA as a solvent in the presence of a cation exchange resin in a series multistage reactor, wherein the reaction temperature in each reaction vessel of the series multistage reactor is adjusted to not more than 65° C., a part of the reaction mixture in the outlet of the first reaction vessel (referred to hereinafter as the outlet reaction mixture) is returned to the inlet portion of the first reaction vessel at a circulation ratio of 1.8 to 10, and the weight ratio of the tertiary butyl alcohol to the liquefied gas in the inlet portion of the first reaction vessel is 0.5 to 3.5.

DETAILED DESCRIPTION OF THE PREFERRED EMBODIMENTS

Figure 1:
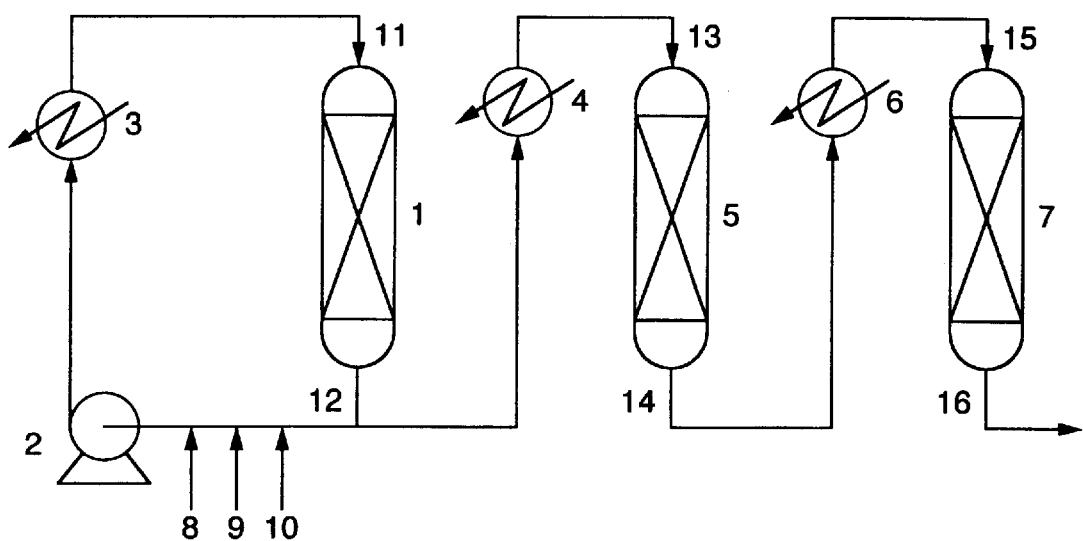
FIG. 1 is an example of the process for carrying out this invention.

As the series multistage reactor used in this invention, there can be employed all types of reactors in which solid-liquid contact is possible, and the type is not critical. As the series multistage reactor used in this invention, there are mentioned, for example, those in which fixed bed type reaction vessels of a continuous flow system are arranged in series, and the like.

The cation exchange resin used in this invention is a strongly acidic cation exchange resin. The cation exchange resin is preferably porous, and as such a cation exchange resin, there are mentioned, for example, Lewatit (trade name of Bayer), Amberlyst (trade name of Rohm & Haas) and the like.

In this invention, the TBA which is a solvent is contained in the circulating liquid of the outlet reaction mixture of the first reaction vessel as described hereinafter and, in addition, TBA may also be freshly added from the exterior. As the TBA freshly added from the exterior, it is convenient to use those obtained by the production process of this invention; however, TBA prepared separately can also be used. The fresh addition of TBA from the exterior to the first reaction vessel has an effect of inhibiting the adiabatic temperature elevation in the second and subsequent reaction vessels.

As the isobutylene source which is the starting material for the reaction, a liquefied gas composed of isobutylene per se or an isobutylene-containing hydrocarbon (referred to hereinafter merely as the liquefied gas) can be used. The isobutylene-containing hydrocarbon includes isobutylene-containing mixtures of butenes, butanes and the like; etc. Industrially, as the isobutylene source, there are used $C_4$ hydrocarbon mixtures obtained by thermal cracking, steam cracking, catalytic cracking or the like of petroleum, preferably those from which butadiene has been separated off. The concentration of isobutylene in the $C_4$ hydrocarbon mixtures is not critical; however, the isobutylene concentrations of commercially available $C_4$ hydrocarbon mixtures are usually not more than 80% by weight. Those $C_4$ hydrocarbon mixtures which are generally easily available and have an isobutylene concentration of 15 to 50 weight % are preferably used as the isobutylene source.

In this invention, a part of the TBA produced in the first reaction vessel is utilized as a solvent by returning a part of the outlet reaction mixture of the first reaction vessel in the series multistage reactor to the inlet portion of the first reaction vessel at a circulation ratio of 1.8 to 10, preferably 2 to 5. As far as this circulation ratio is satisfied, even when the amount of the TBA freshly added from the exterior is small or nil, it is possible to approach the reaction liquid in the inlet portion of the first reaction vessel to a homogeneous composition. Moreover, the circulation of the outlet reaction mixture of the first reaction vessel has an effect of inhibiting the adiabatic temperature elevation in the first reaction vessel due to the hydration reaction between isobutylene and water which is an exothermic reaction. When the circulation ratio is less than 1.8, there is a problem that no sufficient reaction rate is obtained. When the circulation ratio exceeds 10, there is a problem that the difference between the concentration in the inlet and the concentration in the outlet in each reaction vessel becomes nil, the reaction rate is lowered, and the amount of the liquid circulating in the reaction vessel becomes large, so that the equipment becomes excessively large.

Incidentally, in this invention, the circulation ratio when a part of the outlet reaction mixture of the first reaction vessel is returned to the inlet portion of the first reaction vessel is defined as follows:

Circulation ratio=(returned amount)/(amount of starting material fed+amount of TBA fed)

wherein the returned amount is the amount of the outlet reaction mixture of the first reaction vessel returned per unit time; the amount of the starting material fed is the total of the amounts of water and isobutylene or isobutylene-containing hydrocarbon fed per unit time; and the amount of TBA fed is the amount of TBA freshly added from the exterior per unit time which does not include the TBA contained in the circulating liquid. These are all on the weight basis.

In this invention, the weight ratio of TBA to the liquefied gas in the inlet portion of the first reaction vessel is 0.5 to 3.5, preferably 0.8 to 3. By adjusting the circulation ratio and the amount of TBA freshly added from the exterior so as to obtain such a weight ratio, a reaction rate which can be sufficiently satisfied in industry is obtained even when the reaction liquid is heterogeneous. When the weight ratio of TBA to the liquefied gas is less than 0.5, no sufficient reaction rate is obtained, and when it exceeds 3.5, a large amount of TBA is fed to the first reaction vessel, so that there is a problem in respect of reaction equilibrium and the equipment becomes excessively large. The above weight ratios are not desirable.

The necessary weight ratio of TBA to the liquefied gas in the inlet portion of the first reaction vessel can also be achieved by adjusting only the amount of TBA freshly added from the exterior without returning a part of the outlet reaction mixture of the first reaction vessel to the inlet portion of the first reactor; however, since the TBA-synthesis reaction by hydration reaction between isobutylene and water is an equilibrium reaction, the addition of TBA which is the product in a large amount from the exterior to the reaction system has a problem in respect of equilibrium.

In this invention, the reaction temperatures in all the reaction vessels are not more than 65° C. Here, the reaction temperature refers to the temperature of the portion having the highest temperature in each of the reaction vessels. When the reaction temperature is elevated, it follows that the reaction rates of a hydration reaction between isobutylene and water and a side reaction such as dimerization of isobutylene and the like become high. When the reaction temperature exceeds 65° C., the production rate of isobutylene dimer becomes high relatively to the production rate of TBA based on the difference between the temperature-dependencies of the reaction rates, so that there is such a problem that the amount of isobutylene dimer produced as a by-product increases.

Furthermore, it is preferable that the conversion of isobutylene in the first reaction vessel is at least 50%. When the isobutylene conversion is less than 50%, the amounts of isobutylene dimer produced in the second and subsequent reaction vessels increases.

The reaction pressure is not critical; however, such a pressure is adopted that water and isobutylene or an isobutylene-containing hydrocarbon are liquid at the reaction temperature, and this pressure is usually 2 to 50 kg/cm$^2$G.

This invention is explained below using FIG. 1. Incidentally, FIG. 1 is an example of the process for carrying out this invention.

The starting isobutylene or isobutylene-containing hydrocarbon is fed from a feeding pipe 8 and water is fed from a feeding pipe 9. A part of the outlet reaction mixture of the first reaction vessel 1 is circulated by a pump 2 to be returned to the inlet 11 of the first reaction vessel. The second reaction vessel 5 and the third reaction vessel 7 are of the piston type. The reaction mixture in the third reaction vessel 7 is transferred to a TBA-separating and recovering apparatus, for example, a distillation apparatus or an azeotropic distillation apparatus (not shown in FIG. 1) through the outlet 16 of the third reaction vessel 7 and TBA is recovered therein. A part of the recovered TBA is fed to the first reaction vessel 1 from a feeding pipe 10.

According to the flow chart shown in FIG. 1, TBA was synthesized using an isobutylene-containing hydrocarbon having the composition shown in Table 1. Each reaction vessel was a cylinder-shaped reaction vessel having a diameter of 52.7 mm and an internal volume of 12 liters, and three of the reaction vessels were arranged in series and used. Each of the reaction vessels was filled with 12 liters of a MR type strongly acidic cation exchange resin manufactured by Bayer. In the analysis of the starting isobutylene-containing hydrocarbon and water, the TBA produced and the isobutylene dimer, secondary butyl alcohol and the like produced, which were impurities, a gas chromatograph using a capillary column was employed.

TABLE 1

| Compound | Content |
|---|---|
| Isobutylene | 45.0 weight % |
| Isobutane | 2.5 weight % |
| n-Butane | 10.2 weight % |
| 1-Butene | 28.1 weight % |
| trans-2-Butene | 9.3 weight % |
| cis-2-Butene | 4.9 weight % |

The conversion of isobutylene to TBA (referred to hereinafter merely as the conversion) was calculated by the following equation:

Conversion (%)=(number of moles of isobutylene reacted)/(number of moles of isobutylene fed)×100

Moreover, the production rate (g/hr) of each compound refers to weight in gram unit of the compound produced per one hour.

EXAMPLE 1

To the first reaction vessel were fed the starting isobutylene-containing hydrocarbon at a rate of 2.6 kg/hr and the starting water at a rate of 0.5 kg/hr. Reaction was conducted under the conditions that the reaction temperatures in the first, second and third reaction vessels were 60.2° C., 54.4° C. and 52.0° C., respectively, and the circulation ratio was 3.4 and the TBA obtained as the reaction product was added to the first reaction vessel so that the weight ratio of TBA to liquefied gas in the inlet portion of the first reaction vessel became 0.9. At this time, the conversion in the first reaction vessel was 62.8%.

As a result, the TBA production rate was 1,318.0 g/hr, the isobutylene dimer production rate was 0.2 g/hr, the secondary butyl alcohol production rate was 0.5 g/hr, the conversion was 85.3%, and the amounts of the isobutylene dimer and the secondary butyl alcohol produced were very small.

COMPARATIVE EXAMPLE 1

To the first reaction vessel were fed the starting isobutylene-containing hydrocarbon at a rate of 2.6 kg/hr and the starting water at a rate of 0.5 kg/hr. Reaction was conducted under the conditions that the reaction temperatures in the first, second and third reaction vessels were 50.7° C., 65.9° C. and 50.2° C., respectively, the circulation ratio was 9.5, TBA was not added to the first reaction vessel, and the weight ratio of TBA to liquefied gas in the inlet portion of the first reaction vessel was 0.2. At this time, the conversion in the first reaction vessel was 35.2%.

As a result, the TBA production rate was 1,402.0 g/hr, the isobutylene dimer production rate was 29.8 g/hr, the secondary butyl alcohol production rate was 2.0 g/hr, the conversion was 90.7%, and the amounts of the isobutylene dimer and secondary butyl alcohol produced were large.

EXAMPLE 2

To the first reaction vessel were fed the starting isobutylene-containing hydrocarbon at a rate of 2.6 kg/hr and the starting water at a rate of 0.5 kg/hr. Reaction was conducted under the conditions that the reaction temperatures in the first, second and third reaction vessels were 56.7° C., 50.9° C. and 48.7° C., respectively, the circulation ratio was 4.4, and the TBA obtained as the product was added to the first reaction vessel so that the weight ratio of TBA to liquefied gas in the inlet portion of the first reaction vessel became 2.3. At this time, the conversion in the first reaction vessel was 66.7%.

As a result, the TBA production rate was 1,293.0 g/hr, the isobutylene dimer production rate was 0.5 g/hr, the secondary butyl alcohol production rate was 0.4 g/hr, the conversion was 83.7%, and the amounts of the isobutylene dimer and secondary butyl alcohol produced were small.

COMPARATIVE EXAMPLE 2

To the first reaction vessel were fed the starting isobutylene-containing hydrocarbon at a rate of 2.6 kg/hr and the starting water at a rate of 0.5 kg/hr. Reaction was conducted under the conditions that the reaction temperatures in the first, second and third reaction vessels were 71.1° C., 64.2° C. and 59.9° C., respectively, the circulation ratio was 4.4, the TBA obtained as the product was added to the first reaction vessel so that the weight ratio of TBA to liquefied gas in the inlet portion of the first reaction vessel became 2.2. At this time, the conversion in the first reaction vessel was 64.9%.

As a result, the TBA production rate was 1,229.0 g/hr, the isobutylene diner production rate was 1.5 g/hr, the secondary butyl alcohol production rate was 1.6 g/hr, and the conversion was 79.6%.

EXAMPLE 3

Reaction was conducted in the same manner as in Example 1, except that the reaction temperatures in the first, second and third reaction vessels were changed to 60.2° C., 56.0° C. and 52.0° C., respectively, and the circulation ratio was changed to 1.8. At this time, the conversion in the first reaction vessel was 60.2%.

As a result, the TBA production rate was 1318.0 g/hr, the isobutylene diner production rate was 0.4 g/hr, the secondary butyl alcohol production rate was 0.5 g/hr, the conversion was 85.3% and the amounts of the isobutylene dimer and the secondary butyl alcohol produced were small.

EXAMPLE 4

Reaction was conducted in the same manner as in Example 1, except that the reaction temperatures in the first, second and third reaction vessels were changed to 60.2° C., 55.0° C. and 52.0° C., respectively, and the circulation ratio was changed to 2. At this time, the conversion in the first reaction vessel was 60.8%.

As a result, the TBA production rate was 1318.0 g/hr, the isobutylene dimer production rate was 0.3 g/hr, the secondary butyl alcohol production rate was 0.5 g/hr, the conversion was 85.3%, and the amounts of the isobutylene dimer and secondary butyl alcohol produced were very small.

EXAMPLE 5

Reaction was conducted in the same manner as in Example 1, except that the reaction temperatures in the first, second and third reaction vessels were changed to 60.2° C., 54.0° C. and 52.0° C., respectively, and the circulation ratio was changed to 4. At this time, the conversion in the first reaction vessel was 63.6%.

As a result, the TBA production rate was 1318.0 g/hr, the isobutylene dimer production rate was 0.2 g/hr, the secondary butyl alcohol production rate was 0.5 g/hr, the conversion was 85.3%, and the amounts of the isobutylene dimer and secondary butyl alcohol produced were very small.

EXAMPLE 6

Reaction was conducted in the same manner as in Example 1, except that the reaction temperatures in the first, second and third reaction vessels were changed to 60.2° C., 53.0° C. and 52.0° C., respectively, and the circulation ratio was changed to 10. At this time, the conversion in the first reaction vessel was 66.1%.

As a result, the TBA production rate was 1318.0 g/hr, the isobutylene dimer production rate was 0.2 g/hr, the secondary butyl alcohol production rate was 0.5 g/hr, the conversion was 85.3%, and the amounts of the isobutylene dimer and secondary butyl alcohol produced were very small.

COMPARATIVE EXAMPLE 3

Reaction was conducted in the same manner as in Example 1, except that the reaction temperatures in the first, second and third reaction vessels were changed to 60.2° C., 57.0° C. and 52.0° C., respectively, and the circulation ratio was changed to 1.0. At this time, the conversion in the first reaction vessel was 55.0%.

As a result, the TBA production rate was 1318.0 g/hr, the isobutylene dimer production rate was 1.0 g/hr, the secondary butyl alcohol production rate was 1.2 g/hr, and the conversion was 85.3%. Thus, the isobutylene dimer production rate was high.

COMPARATIVE EXAMPLE 4

Reaction was conducted in the same manner as in Example 1, except that the reaction temperatures in the first, second and third reaction vessels were changed to 60.2° C., 53.0° C. and 52.0° C., respectively, and the circulation ratio was changed to 2.0. At this time, the conversion in the first reaction vessel was 66.7%.

As a result, the TBA production rate was 1318.0 g/hr, the isobutylene dimer production rate was 0.2 g/hr, the secondary butyl alcohol production rate was 0.5 g/hr, and the conversion was 85.3%. However, it was necessary to replace the recycling pump by a pump having a larger volume than in Example 1.

INDUSTRIAL APPLICABILITY

According to this invention, TBA can be produced at a high yield by a simple process while the amounts of isobutylene dimer and secondary butyl alcohol produced as by-products are kept small.

What is claimed is:

1. A process for continuously producing tertiary butyl alcohol from water and a liquefied gas comprising isobutylene or an isobutylene-containing hydrocarbon using tertiary butyl alcohol as a solvent which process comprises reacting said water and said liquified gas in the presence of a cation exchange resin in a series multi-stage reactor, wherein the reaction temperature in each reaction vessel of the series multistage reactor is adjusted to not more than 65° C., and wherein a part of the reaction mixture in the outlet of the first reaction vessel is returned to the inlet portion of the first reaction vessel at a circulation ratio of 1.8 to 10, and wherein the weight ratio of the tertiary butyl alcohol to the liquefied gas in the inlet portion of the first reaction vessel is 0.5 to 3.5.

2. The process of claim 1, wherein the cation exchange resin is a strongly acidic cation exchange resin.

3. The process of claims 2, wherein said strongly acidic cation exchange resin is porous.

4. The process of claim 1, wherein the isobutylene-containing hydrocarbon comprises a $C_4$ hydrocarbon mixture obtained by thermal cracking, steam cracking or catalytic cracking of petroleum.

5. The process of claim 4, wherein butadiene has been removed from said $C_4$ hydrocarbon mixture.

6. The process of claim 4, wherein said $C_4$ hydrocarbon mixture has an isobutylene concentration of from 15 to 50 wt. %.

7. The process of claim 1, wherein said circulation ratio is from 2 to 5.

8. The process of claim 1, wherein the weight ratio of the tertiary butyl alcohol to the liquefied gas in the inlet portion of the first reaction vessel is from 0.8 to 3.

9. The process of claim 1, wherein tertiary butyl alcohol is produced at a conversion of at least 79.6%.

10. The process of claim 1, wherein for each 1,293.0–1,318.0 g/hr of tertiary butyl alcohol produced, 0.2–0.5 g/hr of isobutylene dimer and 0.4–0.5 g/hr of secondary butyl alcohol are produced.

* * * * *